United States Patent
Kiukkonen

(10) Patent No.: US 10,542,075 B2
(45) Date of Patent: Jan. 21, 2020

(54) METHOD AND APPARATUS FOR CONFIGURATION FOR MONITORING PATIENT INFORMATION

(71) Applicant: Nokia Technologies Oy, Espoo (FI)

(72) Inventor: Niko Tapani Kiukkonen, Veikkola (FI)

(73) Assignee: NOKIA TECHNOLOGIES OY, Espoo (FI)

( * ) Notice: Subject to any disclaimer, the term of this patent is extended or adjusted under 35 U.S.C. 154(b) by 323 days.

(21) Appl. No.: 15/051,988

(22) Filed: Feb. 24, 2016

(65) Prior Publication Data

US 2017/0242968 A1     Aug. 24, 2017

(51) Int. Cl.
*H04L 29/08* (2006.01)
*H04L 29/06* (2006.01)

(52) U.S. Cl.
CPC .......... *H04L 67/10* (2013.01); *H04L 63/102* (2013.01)

(58) Field of Classification Search
CPC .... H04L 63/102; H04L 67/10; G06F 19/3412
See application file for complete search history.

(56) References Cited

U.S. PATENT DOCUMENTS

| 8,625,618 | B2 * | 1/2014 | Kim | A61B 5/00 370/401 |
| 9,028,407 | B1 * | 5/2015 | Bennett-Guerrero | A61B 5/1121 600/301 |
| 9,153,112 | B1 * | 10/2015 | Kiani | G08B 13/22 |
| 9,439,566 | B2 * | 9/2016 | Arne | A61B 5/0022 |
| 9,526,420 | B2 * | 12/2016 | Fish | G08C 17/02 |

(Continued)

FOREIGN PATENT DOCUMENTS

| EP | 1 855 221 A2 | 11/2007 |
| EP | 2 881 875 A2 | 6/2015 |
| WO | WO 2014 021873 A1 | 2/2014 |

OTHER PUBLICATIONS

International Search Report and Written Opinion for Application No. PCT/FI2017/050113 dated Jun. 12, 2017.

(Continued)

*Primary Examiner* — Blake J Rubin
(74) *Attorney, Agent, or Firm* — Alston & Bird LLP

(57) ABSTRACT

A method, apparatus and computer program product are provided to facilitate reconfiguration of a patient monitoring device. In one method, an indication of an anticipated utilization of a patient monitoring device for which the patient monitoring device is not configured is received. The method also includes accessing device configuration information relating to a configuration associated with the anticipated utilization and causing provision of the device configuration information relating to the configuration associated with the anticipated utilization. In another method, information regarding a configuration of a patient monitoring device is received. The method also determines whether to differently configure the patient monitoring device in accordance with an anticipated utilization of the patient monitoring device for which the patient monitoring device is not configured. If the patient monitoring device is to be differently configured, the method causes information related to the configuration associated with the anticipated utilization to be provided.

20 Claims, 7 Drawing Sheets

(56) References Cited

U.S. PATENT DOCUMENTS

| | | | |
|---|---|---|---|
| 9,596,989 B2* | 3/2017 | Morris | A61B 5/0002 |
| 9,642,529 B1* | 5/2017 | Siddiqui | A61B 5/0008 |
| 10,206,621 B2* | 2/2019 | Zhang | A61B 5/6807 |
| 2003/0028082 A1* | 2/2003 | Thompson | A61B 5/0002 600/300 |
| 2004/0111045 A1* | 6/2004 | Sullivan | A61B 5/11 600/595 |
| 2005/0148890 A1* | 7/2005 | Hastings | A61B 5/0006 600/509 |
| 2006/0026205 A1 | 2/2006 | Butterfield | |
| 2006/0106649 A1 | 5/2006 | Eggers et al. | |
| 2007/0135866 A1* | 6/2007 | Baker | A61B 5/0002 607/60 |
| 2007/0271115 A1 | 11/2007 | Baldus et al. | |
| 2008/0281168 A1* | 11/2008 | Gibson | A61B 5/0205 600/301 |
| 2009/0063187 A1* | 3/2009 | Johnson | A61B 5/411 705/2 |
| 2009/0069642 A1* | 3/2009 | Gao | A61B 5/02055 600/300 |
| 2009/0156988 A1* | 6/2009 | Ferren | A61B 5/0031 604/65 |
| 2010/0033331 A1* | 2/2010 | Bautovich | A61B 5/1116 340/573.1 |
| 2010/0121227 A1* | 5/2010 | Stirling | A61B 5/1127 600/595 |
| 2010/0137945 A1* | 6/2010 | Gadagkar | A61B 5/055 607/60 |
| 2010/0234695 A1* | 9/2010 | Morris | A61B 5/0002 600/300 |
| 2010/0234718 A1* | 9/2010 | Sampath | A61B 5/411 600/407 |
| 2010/0298656 A1* | 11/2010 | McCombie | G16H 50/50 600/301 |
| 2010/0312188 A1* | 12/2010 | Robertson | A61B 5/0006 604/156 |
| 2011/0040197 A1* | 2/2011 | Welch | A61B 5/0205 600/509 |
| 2011/0047298 A1 | 2/2011 | Eaton et al. | |
| 2011/0161100 A1* | 6/2011 | Peak | G06Q 40/08 705/2 |
| 2011/0167250 A1* | 7/2011 | Dicks | A61B 5/1112 713/2 |
| 2012/0003933 A1* | 1/2012 | Baker | H04W 4/029 455/41.2 |
| 2012/0108917 A1* | 5/2012 | Libbus | A61B 5/0006 600/301 |
| 2012/0191147 A1* | 7/2012 | Rao | A61B 5/1171 607/3 |
| 2012/0259652 A1* | 10/2012 | Mallon | G06F 19/3418 705/2 |
| 2012/0317024 A1* | 12/2012 | Rahman | G01K 13/002 705/42 |
| 2013/0117696 A1* | 5/2013 | Robertson | G06F 19/3418 715/763 |
| 2013/0231711 A1* | 9/2013 | Kaib | G06F 19/3418 607/5 |
| 2013/0262155 A1* | 10/2013 | Hinkamp | G06Q 40/08 705/4 |
| 2013/0281801 A1* | 10/2013 | Proud | H01F 38/14 600/301 |
| 2014/0058755 A1* | 2/2014 | Macoviak | G06F 19/328 705/3 |
| 2014/0085082 A1* | 3/2014 | Lyon | A61B 5/746 340/539.12 |
| 2014/0180595 A1* | 6/2014 | Brumback | A61B 5/0015 702/19 |
| 2014/0206976 A1* | 7/2014 | Thompson | A61B 5/0006 600/391 |
| 2014/0243612 A1* | 8/2014 | Li | A61B 5/0205 600/301 |
| 2014/0273858 A1* | 9/2014 | Panther | A61B 5/0002 455/41.2 |
| 2014/0304773 A1* | 10/2014 | Woods | H04L 63/08 726/3 |
| 2014/0316792 A1* | 10/2014 | Siddiqui | G06F 19/3418 705/2 |
| 2014/0365654 A1* | 12/2014 | Huerto | H04L 67/12 709/225 |
| 2014/0378794 A1* | 12/2014 | Conrad | A61B 5/681 600/317 |
| 2015/0119728 A1* | 4/2015 | Blackadar | A61B 5/7264 600/484 |
| 2015/0164351 A1* | 6/2015 | He | A61B 5/1171 702/19 |
| 2015/0223705 A1* | 8/2015 | Sadhu | G01S 19/17 600/301 |
| 2015/0223731 A1* | 8/2015 | Sahin | A61B 5/16 600/301 |
| 2015/0251074 A1* | 9/2015 | Ahmed | A61B 5/02405 700/91 |
| 2015/0310444 A1* | 10/2015 | Chen | G06Q 20/4016 705/44 |
| 2015/0335288 A1* | 11/2015 | Toth | A61B 5/6833 600/373 |
| 2015/0371004 A1 | 12/2015 | Jones | |
| 2016/0029890 A1* | 2/2016 | Stump | G16H 50/30 600/301 |
| 2016/0057565 A1* | 2/2016 | Gold | H04W 4/008 455/41.1 |
| 2016/0058287 A1* | 3/2016 | Dyell | A61B 5/0024 340/870.07 |
| 2016/0072802 A1* | 3/2016 | Hoyos | G06F 17/30867 726/5 |
| 2016/0073904 A1* | 3/2016 | Raglund | A61B 5/0024 600/483 |
| 2016/0095550 A1* | 4/2016 | Lin | A61B 5/6831 600/300 |
| 2016/0127928 A1* | 5/2016 | McClure | H04W 4/008 455/425 |
| 2016/0206242 A1* | 7/2016 | Esposito | A61B 5/1038 |
| 2016/0242646 A1* | 8/2016 | Obma | A61B 5/0024 |
| 2016/0249174 A1* | 8/2016 | Patel | G01K 13/002 |
| 2016/0267310 A1* | 9/2016 | AlNasser | G06K 7/10009 |
| 2016/0278652 A1* | 9/2016 | Kaib | H04W 4/029 |
| 2016/0324472 A1* | 11/2016 | Kaskoun | A61B 5/6833 |
| 2016/0328529 A1* | 11/2016 | Kaib | G06F 19/00 |
| 2016/0342761 A1* | 11/2016 | Whiting | G16H 10/65 |
| 2017/0011210 A1* | 1/2017 | Cheong | H04W 12/06 |
| 2017/0020461 A1* | 1/2017 | Quinn | A61B 5/7275 |
| 2017/0032648 A1* | 2/2017 | McClain | G08B 21/043 |
| 2017/0181645 A1* | 6/2017 | Mahalingam | A61B 5/0004 |
| 2017/0340209 A1* | 11/2017 | Klaassen | A61B 5/681 |
| 2018/0014790 A1* | 1/2018 | Falck | A61B 5/7203 |
| 2018/0042513 A1* | 2/2018 | Connor | A61B 5/6831 |
| 2019/0022400 A1* | 1/2019 | Kumar | A61B 5/0205 |

OTHER PUBLICATIONS

Extended European Search Report for Application No. 17755881.4 dated Aug. 6, 2019.

* cited by examiner

METHOD AND APPARATUS FOR CONFIGURATION FOR MONITORING PATIENT INFORMATION

TECHNOLOGICAL FIELD

Example embodiments relate generally to the configuration of patient monitoring devices such that patient information is provided seamlessly even as the manner in which the patient monitoring device is utilized is changed.

BACKGROUND

Medical professionals frequently need to monitor various parameters to assess and monitor the health of their patients. As such, patient monitoring devices may be utilized in order to monitor various patient-related parameters.

Frequently, a patient will be moved from one department or unit of a hospital or other medical facility to another department or unit for continued treatment. For example, a patient may move from the emergency room to the operating room to a recovery unit and, in turn, to a post-op unit during the course of several days. Some patient monitoring devices are capable of measuring the patient-related parameters that are of importance in each or a number of the different departments or units of a hospital or other medical facility. In some instances, the same patient monitoring device may therefore remain with the patient as the patient moves throughout a hospital. However, the actual patient-related parameters that are of interest may vary from one department or unit to another. Thus, the patient monitoring devices must generally be manually reconfigured in conjunction with the transfer of a patient from one department or unit to another, thereby resulting in additional work on behalf of the medical professionals attending to the patient.

Some patient monitoring devices are also capable of being attached to different body parts and correspondingly monitoring different patient-related parameters. For example, the same patient monitoring device may first be attached to a patient's upper arm and subsequently attached to the leg of the patient. However, the patient-related parameters that are of interest may vary depending upon the body part upon which the patient monitoring device is attached. Thus, the patient monitoring devices must generally be manually reconfigured in conjunction with the body part to which the patient monitoring device is attached, thereby similarly resulting in additional work on behalf of the medical professionals attending to the patient.

BRIEF SUMMARY

A method, apparatus and computer program product are provided in accordance with an example embodiment in order to facilitate the reconfiguration of a patient monitoring device. For example, the method, apparatus and computer program product may be configured to reconfigure the patient monitoring device in an instance in which the patient is transferred to a different environment, such as a different department or unit, within a hospital or other medical facility or in an instance in which the patient monitoring device is attached to a different body part. By facilitating the reconfiguration of the patient monitoring device, the method, apparatus and computer program product of an example embodiment may reduce the effort that must otherwise be expended by medical professionals to manually reconfigure the patient monitoring device.

In accordance with an example embodiment, a method is provided that includes receiving an indication of an anticipated utilization of a patient monitoring device for which the patient monitoring device is not configured. The method also includes accessing device configuration information relating to a configuration associated with the anticipated utilization of the patient monitoring device. The method further includes causing provision of the device configuration information relating to the configuration associated with the anticipated utilization of the patient monitoring device.

The method of an example embodiment receives the indication of the anticipated utilization of the patient monitoring device by receiving an indication of an environment in which the patient monitoring device is located, an indication of a body part of a patient to which the patient monitoring device is attached or information that defines the device configuration information that is to be provided. In an example embodiment, the method further includes determining access rights to data generated by the patient monitoring device subsequently operating in accordance with the device configuration information and providing an indication of the access rights. The method of an example embodiment causes provision of the device configuration information by causing provision of information that defines one or more of measurement parameters to be monitored by the patient monitoring device, measurement intervals at which the measurement parameters are to be monitored by the patient monitoring device or alert limits based upon the measurement parameters to be monitored by the patient monitoring device. In an example embodiment, the method accesses device configuration information by accessing cloud entity that stores and/or defines device configuration information for a plurality of different configurations.

In another example embodiment, an apparatus is provided that includes at least one processor and at least one memory storing computer program code with the at least one memory and the computer program code configured to, with the processor, cause the apparatus to at least receive an indication of an anticipated utilization of a patient monitoring device for which the patient monitoring device is not configured. The at least one memory and the computer program code are also configured to, with the processor, cause the apparatus to access device configuration information relating to a configuration associated with the anticipated utilization of the patient monitoring device. The at least one memory and the computer program code are further configured to, with the processor, cause the apparatus to cause provision of the device configuration information relating to the configuration associated with the anticipated utilization of the patient monitoring device.

The at least one memory and the computer program code configured to, with the processor, cause the apparatus of an example embodiment to receive the indication of the anticipated utilization of the patient monitoring device by receiving an indication of an environment in which the patient monitoring device is located, an indication of a body part of a patient to which the patient monitoring device is attached or information that defines the device configuration information that is to be provided. In an example embodiment, the at least one memory and the computer program code are further configured to, with the processor, cause the apparatus to determine access rights to data generated by the patient monitoring device subsequently operating in accordance with the device configuration information and provide an indication of the access rights. The at least one memory and the computer program code are configured to, with the processor, cause the apparatus of an example embodiment to cause provision of the device configuration information by causing provision of information that defines one or more of measurement parameters to be monitored by the patient monitoring device, measurement intervals at which the measurement parameters are to be monitored by the patient monitoring device or alert limits based upon the measurement parameters to be monitored by the patient monitoring device. In an example embodiment, the at least one memory and the computer program code are configured to, with the processor, cause the apparatus to access device configuration information by accessing cloud entity that stores and/or defines device configuration information for a plurality of different configurations.

In a further example embodiment, a computer program product is provided that includes at least one non-transitory computer-readable storage medium having computer-executable program code portions stored therein with the computer-executable program code portions including program code instructions that, when executed, cause an apparatus to receive an indication of an anticipated utilization of a patient monitoring device for which the patient monitoring device is not configured. The computer-executable program code portions also include program code instructions that, when executed, cause an apparatus to access device configuration information relating to a configuration associated with the anticipated utilization of the patient monitoring device. The computer-executable program code portions further include program code instructions that, when executed, cause an apparatus to cause provision of the device configuration information relating to the configuration associated with the anticipated utilization of the patient monitoring device.

In yet another example embodiment, an apparatus is provided that includes means for receiving an indication of an anticipated utilization of a patient monitoring device for which the patient monitoring device is not configured. The apparatus also includes means for accessing device configuration information relating to a configuration associated with the anticipated utilization of the patient monitoring device. The apparatus further includes means for causing provision of the device configuration information relating to the configuration associated with the anticipated utilization of the patient monitoring device.

In accordance with an example embodiment, a method is provided that includes receiving information regarding a configuration of a patient monitoring device and determining whether to differently configure the patient monitoring device in accordance with an anticipated utilization of the patient monitoring device for which the patient monitoring device is not configured. In an instance in which the patient monitoring device is to be differently configured, the method also includes causing information related to the configuration associated with the anticipated utilization to be provided.

The method of an example embodiment also includes receiving device configuration information relating to the configuration associated with the anticipated utilization of the patient monitoring device and causing the device configuration information to be provided to the patient monitoring device. In an example embodiment, the device configuration information defines one or more of measurement parameters to be monitored by the patient monitoring device, measurement intervals at which the measurement parameters are to be monitored by the patient monitoring device or alert limits based upon the measurement parameters to be monitored by the patient monitoring device. The method of an example embodiment also includes receiving and subsequently operating in accordance with access rights to data generated by the patient monitoring device subsequently operating in accordance with the device configuration information. In an example embodiment, the method causes the information related to the configuration associated with the anticipated utilization to be provided by causing the information to be provided to a cloud entity that stores and/or defines device configuration information for different configurations of the patient monitoring device or to the patient monitoring device.

In another example embodiment, an apparatus is provided that includes at least one processor and at least one memory storing computer program code with the at least one memory and the computer program code configured to, with the processor, cause the apparatus to at least receive information regarding a configuration of a patient monitoring device. The at least one memory and the computer program code are also configured to, with the processor, cause the apparatus to determine whether to differently configure the patient monitoring device in accordance with an anticipated utilization of the patient monitoring device for which the patient monitoring device is not configured. In an instance in which the patient monitoring device is to be differently configured, the at least one memory and the computer program code are further configured to, with the processor, cause the apparatus to cause information related to the configuration associated with the anticipated utilization to be provided.

The at least one memory and the computer program code are further configured to, with the processor, cause the apparatus of an example embodiment to receive device configuration information relating to the configuration associated with the anticipated utilization of the patient monitoring device and to cause the device configuration information to be provided to the patient monitoring device. In an example embodiment, the device configuration information defines one or more of measurement parameters to be monitored by the patient monitoring device, measurement intervals at which the measurement parameters are to be monitored by the patient monitoring device or alert limits based upon the measurement parameters to be monitored by the patient monitoring device. The at least one memory and the computer program code are further configured to, with the processor, cause the apparatus of an example embodiment to receive and subsequently operate in accordance with access rights to data generated by the patient monitoring device subsequently operating in accordance with the device configuration information. In an example embodiment, the at least one memory and the computer program code are configured to, with the processor, cause the apparatus to cause the information related to the configuration associated with the anticipated utilization to be provided by causing the information to be provided to a cloud entity that stores and/or defines device configuration information for different configurations of the patient monitoring device or to the patient monitoring device.

In accordance with a further example embodiment, a computer program product is provided that includes at least one non-transitory computer-readable storage medium having computer-executable program code portions stored therein with the computer-executable program code portions including program code instructions that, when executed, cause an apparatus to receive information regarding a configuration of a patient monitoring device and to determine whether to differently configure the patient monitoring device in accordance with an anticipated utilization of the patient monitoring device for which the patient monitoring device is not configured. In an instance in which the patient monitoring device is to be differently configured, the computer-executable program code portions also include program code instructions that, when executed, cause an apparatus to cause information related to the configuration associated with the anticipated utilization to be provided.

In accordance with yet another example embodiment, an apparatus is provided that includes means for receiving information regarding a configuration of a patient monitoring device and means for determining whether to differently configure the patient monitoring device in accordance with an anticipated utilization of the patient monitoring device for which the patient monitoring device is not configured. In an instance in which the patient monitoring device is to be differently configured, the apparatus also includes means for causing information related to the configuration associated with the anticipated utilization to be provided.

BRIEF DESCRIPTION OF THE DRAWINGS

Figure 1:
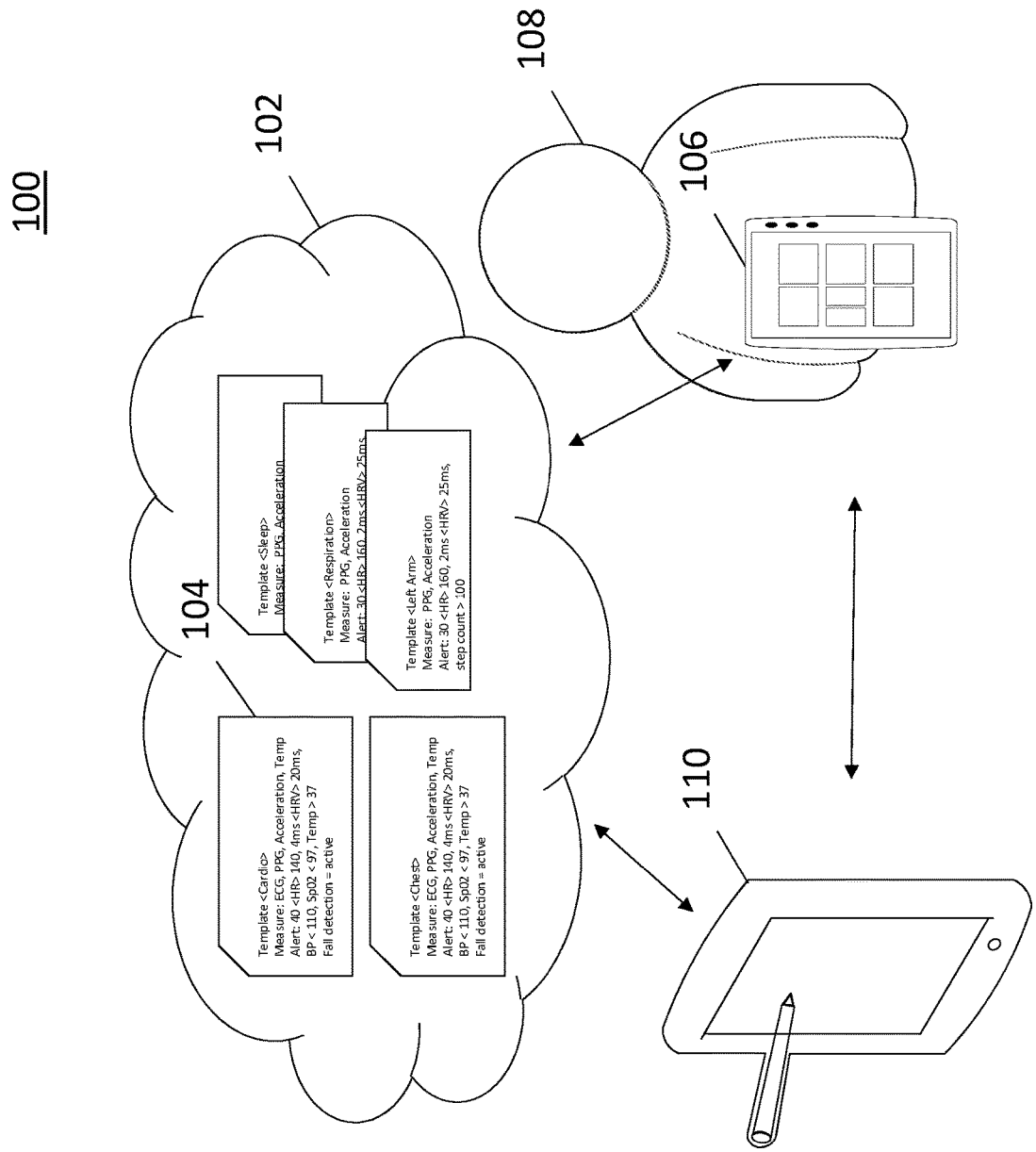
Figure 2:
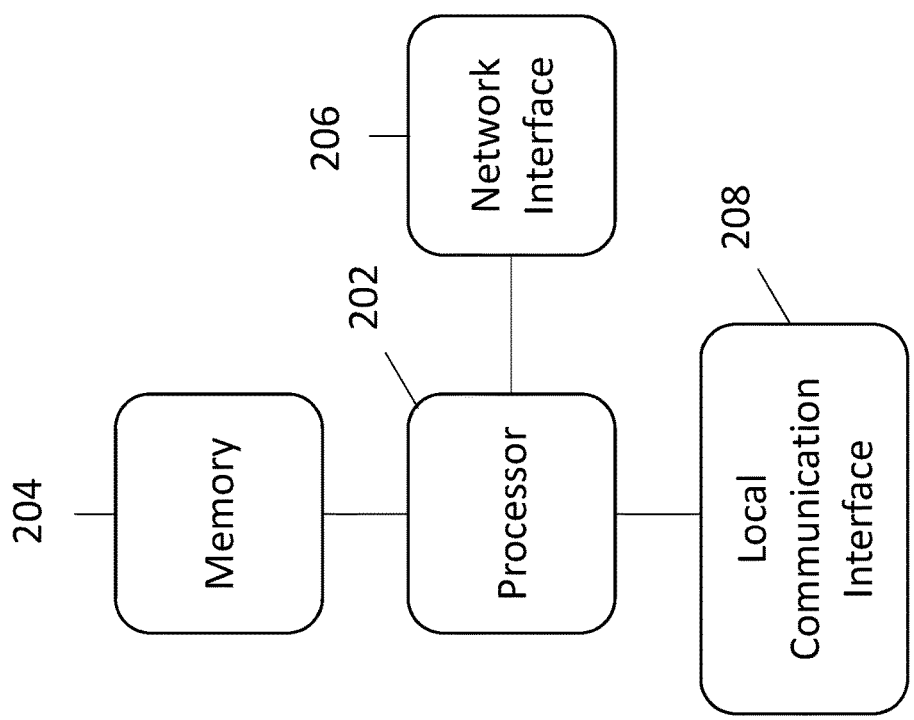
Figure 3:
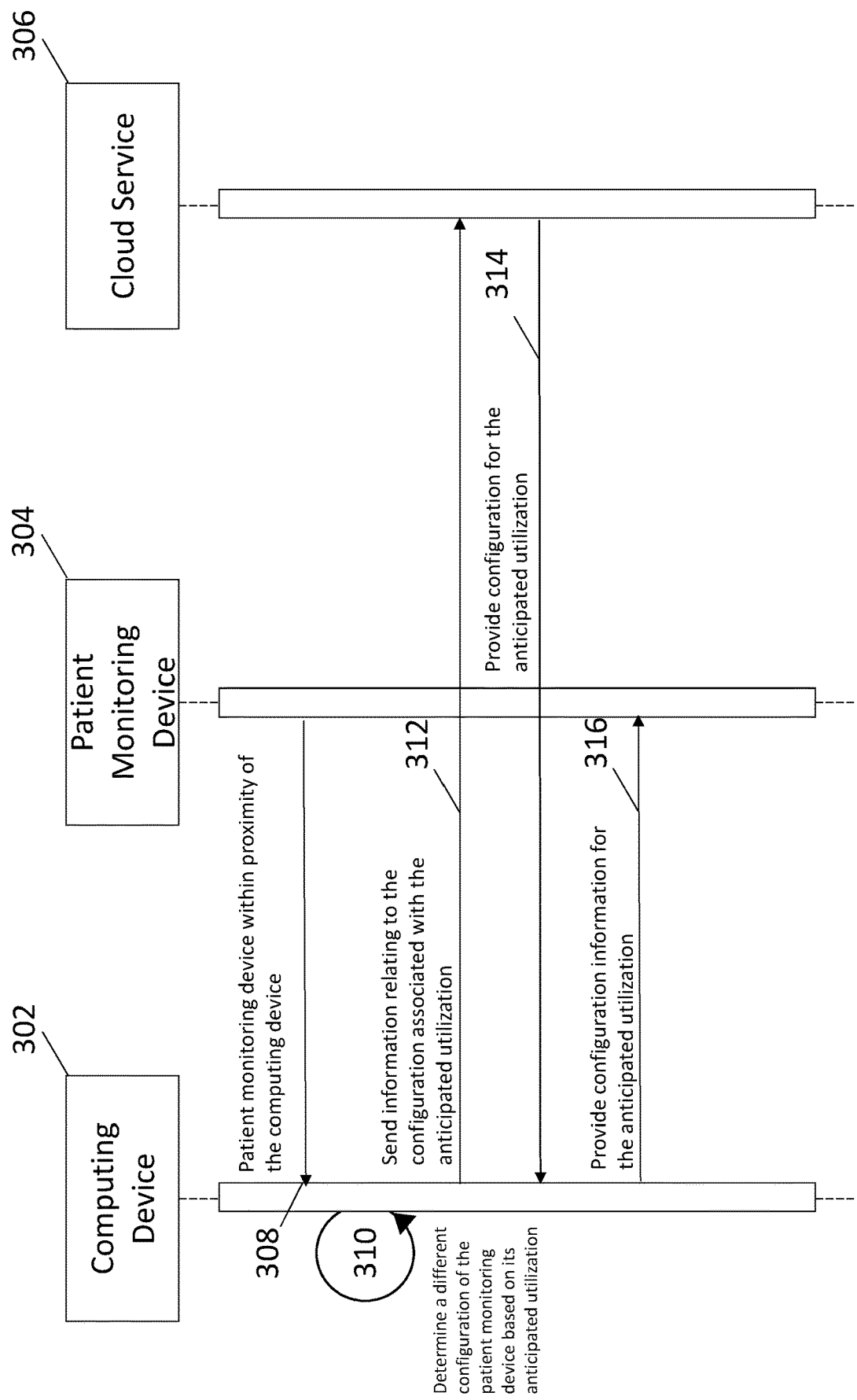
Figure 4A:
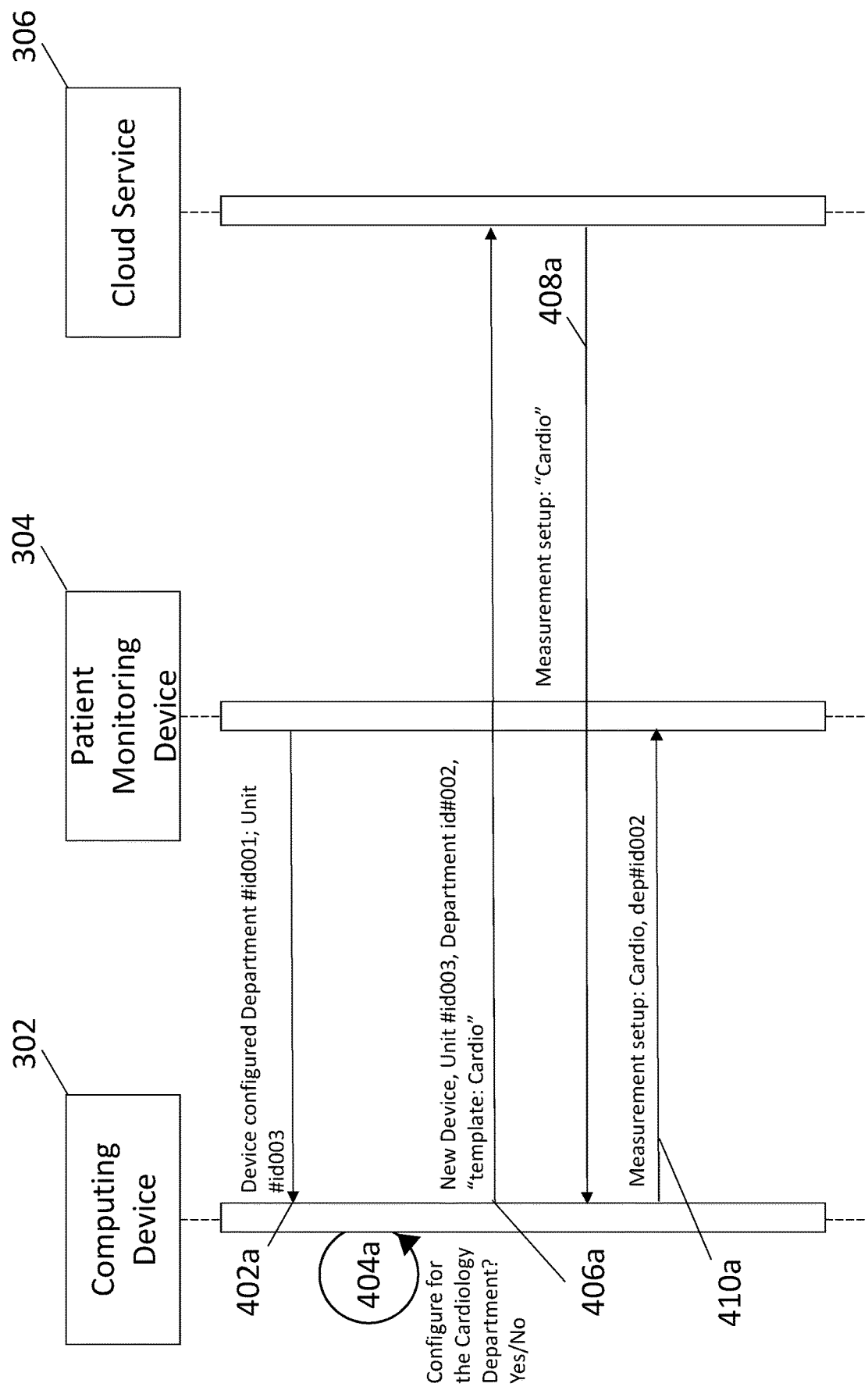
Figure 4B:
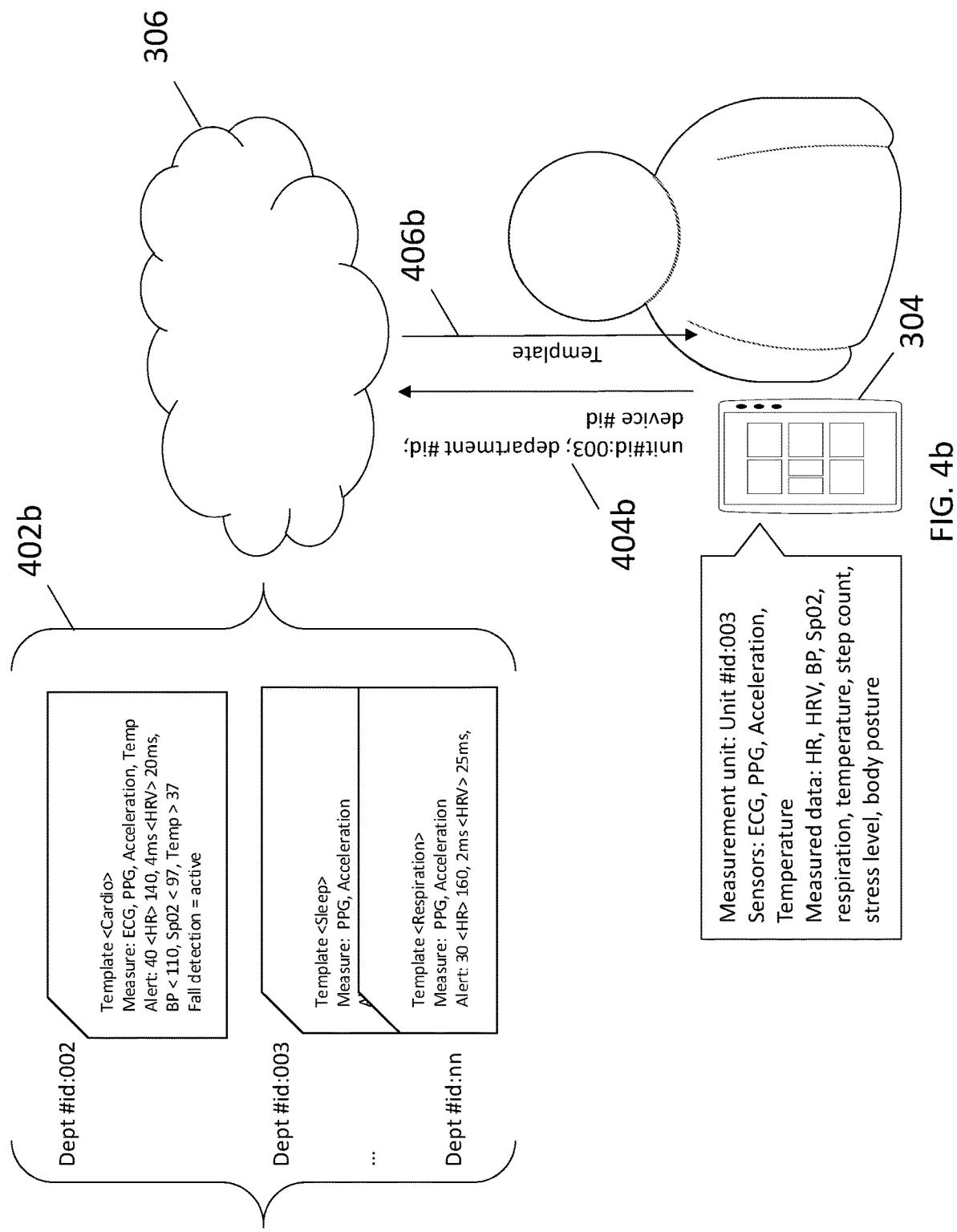
Figure 5A:
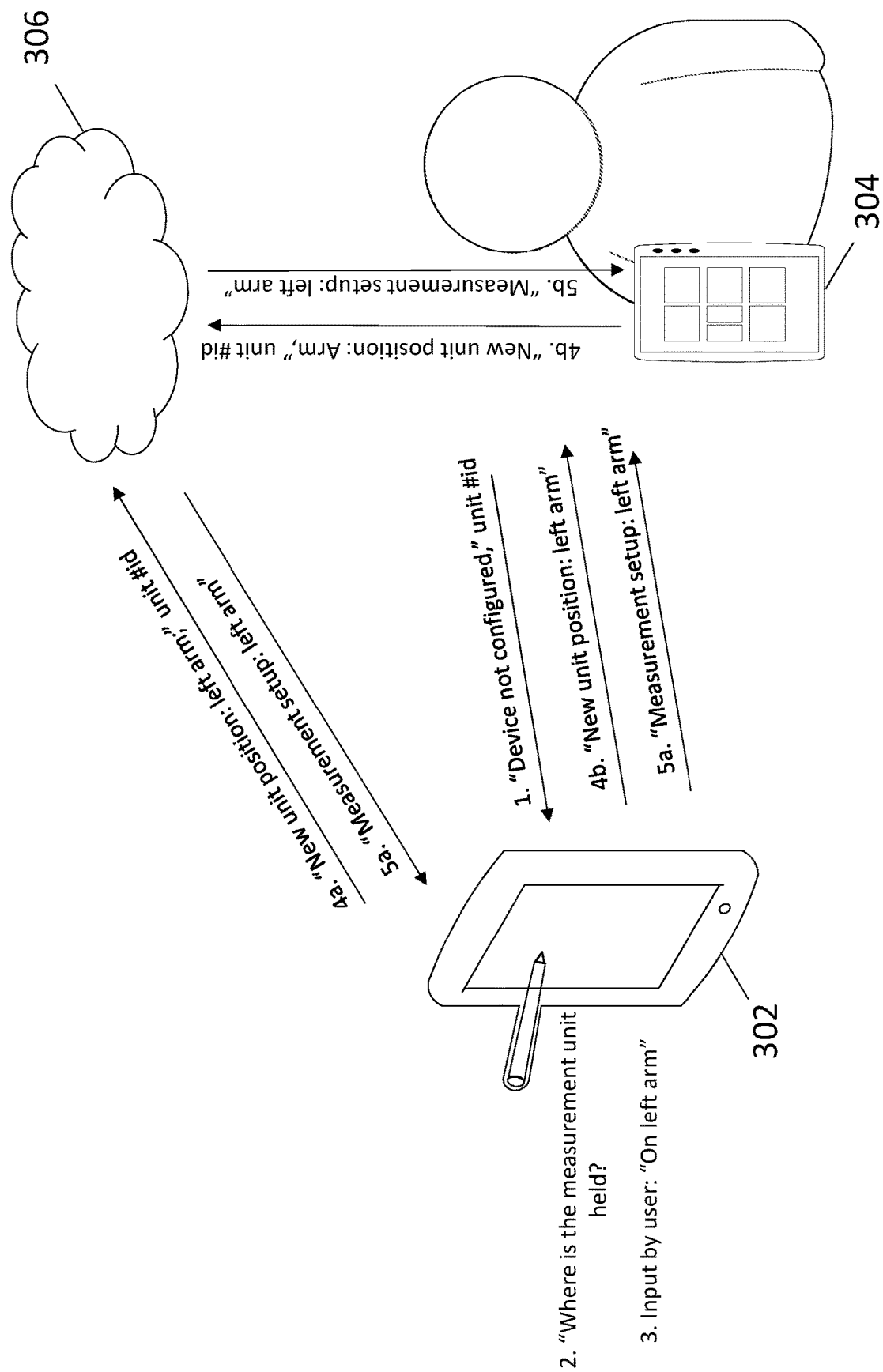
Figure 5B:
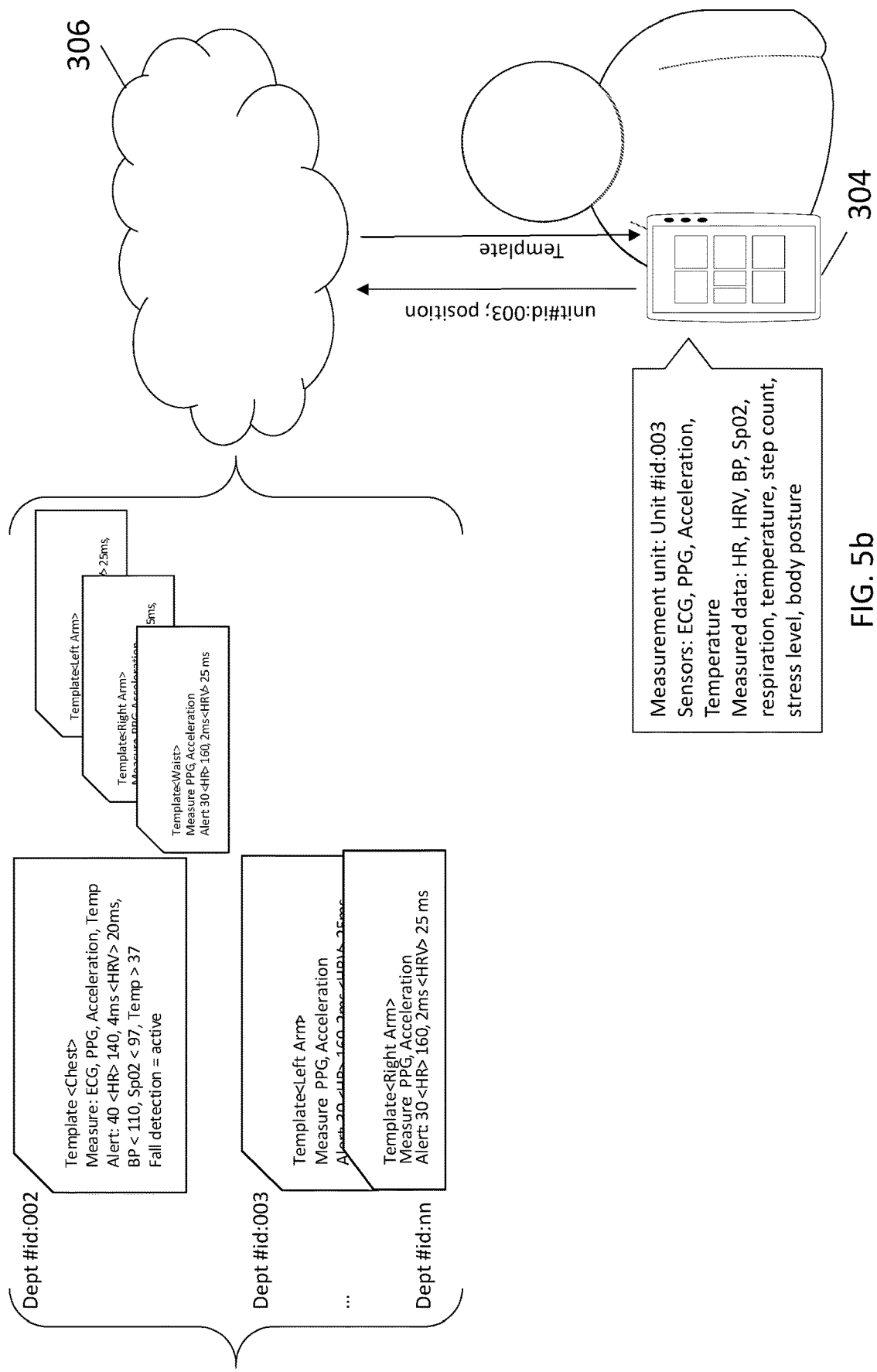

Having thus described certain example embodiments in general terms, reference will hereinafter be made to the accompanying drawings, which are not necessarily drawn to scale, and wherein:

FIG. 1 is a representation of a patient monitoring device, patient measurement unit, and cloud service configured to communicate with one another, such as over a cellular interface, in accordance with an example embodiment of the present invention;

FIG. 2 is a block diagram of an apparatus that may be specifically configured in accordance with an example embodiment of the present invention;

FIG. 3 is a sequence diagram illustrating operations performed, such as by the apparatus of FIG. 2, in accordance with an example embodiment of the present invention;

FIG. 4a is a sequence diagram illustrating operations performed, such as by the apparatus of FIG. 2, for providing measurement setup and configuration in accordance with an example embodiment of the present invention;

FIG. 4b is a representation of the patient measurement unit and the cloud service for providing measurement setup and configuration in accordance with an example embodiment of the present invention;

FIG. 5a is a representation of data flowing through the patient monitoring device, patient measurement unit, and cloud service in accordance with an example embodiment of the present invention; and FIG. 5b is a representation of the patient measurement unit and the cloud service for providing measurement setup and configuration in accordance with an example embodiment of the present invention.

DETAILED DESCRIPTION

Some embodiments will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being transmitted, received and/or stored in accordance with embodiments of the present invention. Thus, use of any such terms should not be taken to limit the spirit and scope of embodiments of the present invention.

Additionally, as used herein, the term 'circuitry' refers to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of 'circuitry' applies to all uses of this term herein, including in any claims. As a further example, as used herein, the term 'circuitry' also includes an implementation comprising one or more processors and/or portion(s) thereof and accompanying software and/or firmware. As another example, the term 'circuitry' as used herein also includes, for example, a baseband integrated circuit or applications processor integrated circuit for a mobile phone or a similar integrated circuit in a server, a cellular network device, other network device, and/or other computing device.

As defined herein, a "computer-readable storage medium," which refers to a non-transitory physical storage medium (e.g., volatile or non-volatile memory device), can be differentiated from a "computer-readable transmission medium," which refers to an electromagnetic signal.

Embodiments of the present disclosure provide for configuring patient monitoring devices based on context, such as location of the department, unit or other environment within which the patient monitoring device is located, and/or the body part to which the patient monitoring device is attached. Furthermore, configuration information is provided, such as via a cloud based service, via templates for each context, such as a location within which the patient monitoring device is located and/or each body part to which the patient monitoring device is attached.

Referring to the FIGS. 1-5b, a system and associated methods incorporating the principles of example embodiments of the instant invention, can be seen in order to facilitate monitoring of a living entity, such as patient monitoring, pet or other animal monitoring or the like. As described below, the system includes patient monitoring devices, such as various medical monitoring devices that are typically used in hospital or other healthcare units/settings to monitor the health of a patient via health care data, such as vital signs, heart rate, blood oxygen saturation, blood pressure, respiration rate, body temperature, electrocardiogram (ECG), and any other clinical data that may be required depending on the patient's condition and the care being provided, but not intended to be exclusive thereof. As also described below, the patient monitoring devices may be of the type that can be deployed throughout any number of departments or units within a hospital or other healthcare facility, but that can be configured to operate specific to a respective department or unit when needed. Additionally or alternatively, the patient monitoring devices may be capable of being attached to different parts of a patient's body, e.g., arm, leg, chest, etc. and, in some embodiments, may be configured to operate specific to the body part to which the patient monitoring device is attached.

FIG. 1 illustrates a system 100 for fulfilling configuration requests, such as may be made by a patient monitoring device or by a computing device of a medical professional who may be responsible for the care of the patient. In an example embodiment, the configuration requests may be made of a cloud service which may be configured to provide device configuration information based upon, for example, the location of the patient monitoring device and/or the body part to which the patient monitoring device is attached. FIG. 1 illustrates an example cloud service 102 used to host measurement setups and configurations for the different hospital functions and departments based on preset measurement configuration templates 104, according to one embodiment of the present invention. In an example embodiment, the cloud service 102 additionally or alternatively hosts measurement setups and configurations based on preset measurement configuration templates for the patient monitoring device as attached to different body parts of the patient 108. The cloud service 102 provides the templates configured for a specific department and/or a specific body part, such as to the patient monitoring device 106 and/or a computing device 110 associated with the patient monitoring device 106. As such, the monitoring device 106 utilizes the new measurement setup in conjunction with subsequent monitoring of the patient 108.

In order to provide patient monitoring functions in situations in which a patient is moved from one department to another without the need for anyone to manually reconfigure and setup the monitoring device 106 while it transits together with the patient through a typical treatment flow, the method and apparatus of an example embodiment are capable of configuring the patient monitoring device, e.g. semi-automatically or automatically, based on the enviornment of the patient monitoring device. The cloud service 102 and the computing device 110 may each include an apparatus 200 as illustrated in FIG. 2 so as to include one or more processors 202, one or more memory devices 204 and a remote network interface 206. The computing device 110 of an example embodiment may also include a local communication interface 208, as shown in FIG. 2, for communicating with the patient monitoring device 106. The patient monitoring device 106 of an example embodiment may also include an apparatus 200 as generally shown in FIG. 2 and, as such, may include one or more processors 202, one or more memory devices 204 and a local communication interface 208 for communicating with the computing device 110. In embodiments in which the patient monitoring device 106 is configured to communicate directly with the cloud service 102, the apparatus 200 embodied by the patient monitoring device 106 may also include a remote network interface 206. Further, the apparatus 200 embodied by the patient monitoring device 106 is configured to include one or more sensors for measuring various parameters associated with the patient monitoring device 106, such as the location and/or orientation of the patient monitoring device. As used herein, a patient is an individual who is being monitored for health care purposes, including the monitoring performed prior to and/or following surgery or an illness, during rehabilitation or other treatment or the like. Additionally, the patient data (also known as patient sensor data) may be any of various types of health care data collected by specific sensors 210 worn by or otherwise monitoring the patient and associated with the patient so as to be utilized in conjunction with the monitoring of the patient for health care purposes.

In some embodiments, the processor 202 (and/or co-processors or any other processing circuitry assisting or otherwise associated with the processor) may be in communication with the memory device 204 via a bus for passing information among components of the apparatus 200. The memory device may be non-transitory and may include, for example, one or more volatile and/or non-volatile memories. In other words, for example, the memory device may be an electronic storage device (e.g., a computer readable storage medium) comprising gates configured to store data (e.g., bits) that may be retrievable by a machine (e.g., a computing device like the processor). The memory device may be configured to store information, data, content, applications, instructions, or the like for enabling the apparatus to carry out various functions in accordance with an example embodiment of the present invention. For example, the memory device could be configured to buffer input data for processing by the processor. Additionally or alternatively, the memory device could be configured to store instructions for execution by the processor.

As described above, the apparatus 200 may be embodied by a patient monitoring device 106, a cloud service 102, such as may, in turn, be embodied by a cloud server, and/or a computing device 110 of a medical professional responsible for the health care of the patient. However, in some embodiments, the apparatus may be embodied as a chip or chip set. In other words, the apparatus may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The apparatus may therefore, in some cases, be configured to implement an embodiment of the present invention on a single chip or as a single "system on a chip." As such, in some cases, a chip or chipset may constitute means for performing one or more operations for providing the functionalities described herein.

The processor 202 may be embodied in a number of different ways. For example, the processor may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor may include one or more processing cores configured to perform independently. A multi-core processor may enable multiprocessing within a single physical package. Additionally or alternatively, the processor may include one or more processors configured in tandem via the bus to enable independent execution of instructions, pipelining and/or multithreading.

In an example embodiment, the processor 202 may be configured to execute instructions stored in the memory device 204 or otherwise accessible to the processor. Alternatively or additionally, the processor may be configured to execute hard coded functionality. As such, whether configured by hardware or software methods, or by a combination thereof, the processor may represent an entity (e.g., physically embodied in circuitry) capable of performing operations according to an embodiment of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform the algorithms and/or operations described herein when the instructions are executed. However, in some cases, the processor may be a processor of a specific device (e.g., a patient monitoring device) configured to employ an embodiment of the present invention by further configuration of the processor by instructions for performing the algorithms and/or operations described herein. The processor may include, among other things, a clock, an arithmetic logic unit (ALU) and logic gates configured to support operation of the processor.

The apparatus 200 also includes one or both of a remote network interface 206 and a local communication interface 208. The remote network interface 206 may be any means such as a device or circuitry embodied in either hardware or a combination of hardware and software that is configured to transmit data to a remote network device, such as a cloud server or a set of servers, such as via a cellular network. As such, the remote network interface 206 may be configured to transmit and receive data via any of a number of different cellular communication techniques such as any of a number of second generation (2G), 2.5G, third generation (3G), fourth generation (4G) or Long Term Evolution (LTE) communication techniques. Although described herein as a cellular connection, various types of remote network connections may be utilized in other embodiments including, for example, a metropolitan area network (MAN), a wide area network (WAN) (e.g., Internet) and/or one or more voice networks, such as a public-switched telephone network (PSTN). Similarly, the local communication interface 208 may be any means such as a device or circuitry embodied in either hardware or a combination of hardware and software that is configured to receive and/or transmit data from/to patient monitoring devices 106 and the computing devices 110 of the medical professionals responsible for the health care of the patients, such as via any of the various proximity based communication techniques, such as in accordance with Bluetooth™ LE (Low Energy), Bluetooth™, IEEE 802.15.4, WiFi, Universal Serial Bus (USB), infrared (IrDA), local area network (LAN) or wireless LAN (WLAN) protocols. The remote network interface and the local communication interface may each include, for example, an antenna (or multiple antennas) and supporting hardware and/or software for enabling communications with a wireless communication network. Additionally or alternatively, the remote network interface and the local communication interface may each include the circuitry for interacting with the antenna(s) to cause transmission of signals via the antenna(s) or to handle receipt of signals received via the antenna(s).

As noted above, the apparatus 200 of the example embodiment may include or otherwise be associated with one or more sensors. The sensors may be configured to measure, monitor or otherwise detect various parameters associated with the patient including, for example, the position of the patient monitoring device 106 of the patient 108. For example, the sensors may include an acceleration sensor input, orientation sensor input, tilting sensor input, altitude sensor input, galvanic skin sensor input, and/or electronic compass input. The apparatus may also include any other types of sensors/devices in other embodiments, such as photoplethysmogram (PPG) sensor, electroencephalography (EEG) sensor, electrocardiography (ECG) sensor, pulse oximetry sensor, and/or blood pressure sensor.

Referring now to FIG. 3, the operations performed, such as by the computing device 302, patient monitoring device 304, and cloud service 306, in order to provide configuration information for the anticipated utilization of the patient monitoring device. As shown in 308, the patient monitoring device 304 includes means, such as the processor 202, the local communication interface 208 or the like, for providing and the computing device 302 includes means, such as the processor, the local communication interface or the like, for receiving an indication of the context of the patient monitoring device, such as the presence and/or location of the patient monitoring device and information regarding the configuration, type, identification and/or network address of the patient monitoring device. The patient monitoring device 304, such as the processor 202, may be configured to determine that the patient monitoring device has been relocated and is now located in a different environment, such as a different department or unit of a hospital or other health care facility, such as a result of the transfer of the patient, in various manners. For example, the patient monitoring device 304 may newly identify the computing device 302, such as by discovering the computing device via a proximity-based communication technique, and may determine the computing device to be associated with a respective department or unit of a hospital or other health care facility, such as based upon an analysis of the device identifier of the computing device. Alternatively, the patient monitoring device 304 may identify the department or unit in which the patient monitoring device is newly located by indoor location techniques, by codes, e.g., Quick Response (QR) codes, Near Field Communication (NFC) tags, etc., that are present in the location that are read by the patient monitoring device or by manual entry or selection of the environment, e.g., department or unit, from a listing of possible locations. Still further, the patient monitoring device 304 may identify the department or unit in which the patient monitoring device is located by satellite location detection techniques, (e.g. a Global Navigation Satellite System (GNSS), Galileo, GPS, assisted GPS (A-GPS)) and/or by mobile based tracking techniques (e.g. cell identification (CELL ID), cellular base station based and/or triangulation) or the like. Once the patient monitoring device 304 has determined that the patient monitoring device has been relocated and is now located in a different environment, e.g., a different department or unit, the patient monitoring device, such as the processor 202, the local communication interface 208 or the like, is configured to notify the computing device 302 of its presence and to provide information regarding its configuration, such as information indicating its current configuration or indicating that it is not currently configured.

Based upon the information regarding configuration that is provided by the patient monitoring device 304, the computing device 302 includes means, such as the processor 202 or the like, for determining whether to differently configure the patient monitoring device as shown in 310. In this regard, the computing device 302, such as the processor 202, is configured to determine whether the configuration of the patient monitoring device 304 is different than the configuration associated with the anticipated utilization of the patient monitoring device. The anticipated utilization of the patient monitoring device 304, such as the measurements to be monitored and the schedule at which the measurements are to be collected as well as the alert limits defining the conditions under which alerts are to be issued, may be defined based upon the environment, e.g., department or unit, in which the patient monitoring device is located. For example, the anticipated utilization of the patient monitoring device 304 in a cardiology unit may be different than the anticipated utilization of the patient monitoring device in an oncology unit. In an instance in which the configuration of the patient monitoring device 304 is different than the configuration associated with the anticipated utilization of the patient monitoring device, the computing device 302, such as the processor 202 or the like, is configured in an example embodiment to query the user as to whether the patient monitoring device should be reconfigured and, in response to user input indicating that the patient monitoring device should be reconfigured, the configuration process of FIG. 3 may continue. Alternatively, the computing device 302 may be configured to proceed with the reconfiguration of the patient monitoring device 304 without querying the user in other embodiments.

In an instance in which the patient monitoring device 304 is to be reconfigured and as shown at 312, the computing device 302 includes means, such as the processor 202, the remote network interface 206, the local communication interface 208 or the like, for causing information related to the configuration associated with the anticipated utilization to be provided, such as to the cloud service 306 as shown in FIG. 3 or the patient monitoring device 304. For example, the computing device 302 may provide information identifying the context, e.g. the anticipated utilization, such as by identifying the environment, e.g., department or unit, within which the patient monitoring device 304 is located and/or identification of the patient monitoring device 304. In an instance in which the computing device 302 provides the information related to the configuration associated with the anticipated utilization to the patient monitoring device 304, the patient monitoring device may, in turn, forward or otherwise provide information related to the configuration associated with the anticipated utilization of the patient monitoring device to the cloud service 306.

From the perspective the cloud service 306, the cloud service, such as the cloud server, includes means, such as the processor 202, the remote network interface 206 or the like, for receiving an indication of the anticipated utilization of the patient monitoring device 304 for which the patient monitoring device is not configured. For example, the indication of the anticipated utilization of the patient monitoring device 304 may be provided by the information related to the configuration associated with the context information, e.g. on anticipated utilization, that is provided by the computing device 302. Further, the context can include information on the type, capabilities, network address and/or sensor configuration of the patient monitoring device 304. Further, the context can include information on the identification of person carrying the device 304. The cloud service 306, such as the cloud server, of this example embodiment also includes means, such as the processor 202, the memory 204 or the like, for accessing device configuration information relating to the configuration associated with the anticipated utilization of the patient monitoring device 304. In this regard, the cloud service 306 may include or have access to device configuration information for each of a plurality of different configurations, such as for the configurations associated with each of the different departments or units of a hospital or other health care facility. The cloud service 306, such as the cloud server, of this example embodiment also includes means, such as the processor 202, the remote network interface 206 or the like, for causing provision of the device configuration information relating to the configuration associated with the anticipated utilization of the patient monitoring device 304 to be provided, such as to the computing device 302 and/or the patient monitoring device.

Returning now to the embodiment depicted in FIG. 3 in which the cloud server 306 provides the device configuration information to the computing device 302 and, in particular, as shown at 314, the computing device also includes means, such as the processor 202, the remote network interface 206 or the like, for receiving device configuration information relating to the configuration associated with the anticipated utilization of the patient monitoring device 304.

As shown at 316, the computing device 302 of this example embodiment also includes means, such as the processor 202, the local communication interface 208 or the like, for causing the device configuration information to be provided to the patient monitoring device 304. Alternatively, the device configuration information can be provided directly to the patient monitoring device 304 from the cloud server 306.

In an example embodiment, the device configuration information is provided in the form of one or more templates. For example, FIG. 1 depicts a plurality of templates 104 stored by the cloud service 102, such as in the memory 204 of the cloud service 102, and selectively provided to the computing device 110 and/or the patient monitoring device 106 based upon the anticipated utilization of the patient monitoring device. Although the template may be configured in various manners, the template of an example embodiment defines one or more of measurement parameters to be monitored by the patient monitoring device 106, measurement intervals at which the measurement parameters are to be monitored by the patient monitoring device or alert limits based upon the measurement parameters to be monitored by the patient monitoring device and the thresholds at which alerts are to be provided, such as via the computing device 110 to the medical professional responsible for the care of the patient.

In addition to providing device configuration information, the cloud service 102 of an example embodiment may include means, such as the processor 202 or the like, for determining access rights to data generated by the patient monitoring device 106 during its subsequent operation in accordance with the device configuration information. The cloud service 102 of this example embodiment also includes means, such as the processor 202, the remote network interface 206 or the like, for providing an indication of the access rights, such as to the computing device 110 and/or the patient monitoring device 106. Similarly, the computing device 110 of this example embodiment includes means, such as the processor 202, the remote network interface 206 or the like, for receiving and subsequently operating in accordance with the access rights. The access rights may define people and/or devices who may be provided access to the various types of data generated by the patient monitoring device 106 while operating in accordance with the device configuration information.

In a more specific example shown in FIG. 4a, the patient monitoring device 304 is configured to utilize either indoor positioning information, self-determined device proximity information, department information entered by medical professionals in the monitoring device, or any other technique to determine the current department or unit within the hospital or other health care facility in which the patient monitoring device is currently located. As an example, shown at 402a, in an instance in which patient monitoring device 304 discovers a different computing device 302, the patient monitoring device may transmit a message to the computing device that provides a patient monitoring device identifier, e.g., Unit #id:003, and an indication of the current configuration of the patient monitoring device, such as an indication of being configured for Department #id:001. As shown at 404a, the computing device 302 may then determine whether the patient monitoring device 304 should be differently configured based upon its anticipated utilization, such as based upon the environment, e.g., department or unit or home setting, with which the computing device is associated. In an instance in which the computing device 302 determines, such as based upon user input, that the patient monitoring device 304 is to be differently configured, the computing device of an example embodiment transmits a message to the cloud service 306 as shown at 406a that indicates the anticipated utilization of the patient monitoring device, such as by providing the patient monitoring device identifier and the department identifier and, in some embodiments, an indication of the template, e.g., Cardio" that defines the device configuration information. Alternatively, the computing device 302 may transmit a message to the patient monitoring device 304 that indicates the anticipated utilization of the patient monitoring device, such as by providing the department identifier and, in some embodiments, an indication of the template, e.g., Cardio" that defines the device configuration information. In this embodiment, the patient monitoring device 304 may, in turn, transmit a message to the cloud service 306 that indicates the anticipated utilization of the patient monitoring device, such as by providing the patient monitoring device identifier and the department identifier.

In an embodiment depicted in FIG. 4a in which the computing device 302 transmits a message to the cloud service 306 informing the cloud service of the anticipated utilization of the patient monitoring device 304, the cloud service may respond by transmitting a message to the computing device that provides the one or more templates appropriate for the anticipated utilization of the patient monitoring device as shown at 408a. The computing device 302 may, in turn, forward one or more templates to the patient monitoring device 304, along with the department identifier, as shown at 410a. Alternatively, in an embodiment in which the patient monitoring device 304 transmits a message to the cloud service 306 informing the cloud service of its anticipated utilization, the cloud service may respond directly to the patient monitoring device by transmitting a message to the patient monitoring device that provides the template appropriate for its anticipated utilization. Alternatively, the one or more templates can be provided directly to the patient monitoring device 304 from the cloud server 306.

The aforementioned implementation provides for configuration of the remote patient monitoring device 304, such as in an automatic fashion, and can be used to adapt the patient monitoring device for use in different environments, e.g., multiple different departments or units within the hospital, while significantly reducing the required workload from medical professionals to re-configure the patient monitoring device, its parameters, and/or access rights to the patient data collected by the patient monitoring device. Thus, the patient monitoring device 304 can seamlessly transfer between different hospital departments and to home. For example, when the patient leaves the hospital, the patient monitoring device 304 can automatically obtain the configuration that is more suitable to the home monitoring use case. For example, the time when alerts or notifications should be raised may be less critical in the home setting than within the hospital setting, thereby permitting the alert limits to be raised and allowing the patient monitoring device 304 to operate in a more battery optimized manner. In addition, the access rights and medical professionals responsible for receiving the alerts and notifications can be matched with the now dispatched, home-based patient, such as in an automatic fashion.

In an example embodiment, the templates may establish configurations that are appropriate for a given environment and particular use such as, for example, at home, when outdoors, during day or night, etc. The templates may provide settings that establish system settings for the designated use in the given environment. As for example, a template may establish that measurements are to be obtained more often in the instance in which an alert threshold has been exceeded for a predefined period of time. It should be appreciated that these example embodiments may improve or optimize the battery operation without compromising measurement accuracy.

In the embodiment of FIG. 4b, the cloud service 306 hosts the measurement unit setups and configurations for the different hospital functions and departments or other settings, such as in the form of different templates 402b. Measured patient parameters, measurement intervals and alert limits can differ between departments of the hospital, such as in the case of a cardiac department compared to an oncological department. It follows that any department can also have multiple different measurement templates configured for that particular department. In order to reduce or eliminate the burden on medical professionals to manually configure all of the parameters of patient monitoring devices every time a new patient enters their department, the preset measurement configuration templates 402b may be stored and selectively provided by the cloud service 306. In alternative implementations, the templates can be also stored in the computing device 302 or in the patient monitoring device 304. As shown in FIG. 4b, in the instance in which the patient monitoring device 304 contacts the cloud service 306 and informs the cloud service of a change of department with a new department identification (ID) as shown at 404b, the cloud service determines the measurement template matching with the department ID and provides the new measurement setup and configuration template associated with the matching department ID to the patient monitoring unit as shown at 406b.

In an example embodiment, the new setup and configuration template may need to be verified by the medical professionals responsible for the treatment of the patient. As part of the same mechanism by which the cloud service identifies the correct template based upon the department or unit in which the patient monitoring device 304 is located, the cloud service 306 may also associate one or more medical professionals with the patient monitoring device from the department or unit in which the patient monitoring device is located. In this regard, the cloud service 306 may maintain, such as in memory 204, a list of the medical professionals operating in the different departments or a list of computing devices 302 used at the different departments. It follows that in the instance when a patient monitoring device 304 enters a different department together with the patient, the access rights for the patient data and the alerts and notifications may be configured, such as by the cloud service 306 to be accessible to the medical professionals (or at least selected ones of the medical professionals) of the department or unit in which the patient monitoring device is now located.

Further, the cloud service may be configured to facilitate user control of at least some functions associated with information or access control of the patient monitoring device (e.g. changing alert limits). In this example embodiment, information may be stored, such as by the cloud service, as to any changes in the operation or access control of the patient monitoring device as well the identity of the person or device who instituted the change.

While the example embodiments have been described with respect to automatically re-configuring the patient monitoring device 304 while it transits together with the patient through the treatment flow though different departments, the method, apparatus and computer program product are not so limited and may be deployed in other settings with the anticipated utilization of the patient monitoring device (and the corresponding device configuration information, e.g., template) being differently determined. For example, the anticipated utilization of the patient monitoring device 304 may be based upon the body part to which the patient monitoring device is attached. As would be apparent to one skilled in the art, the same patient monitoring device 304 may be attached to different body parts in order to collect different parameters. In this regard, the patient monitoring device 304 may employ sensors to calculate, assess, or determine clinical data of the patient, such as, for example, heart rate, sleep efficiency, body temperature, respiration rate, etc. The same patient monitoring device 304 may be enabled to be utilized for multiple different use cases having operational and business benefits such as long term monitoring, short term electrocardiogram (ECG) monitoring, wellness monitoring, elderly care, etc. For example, the same patient monitoring device 304 may be configured to be attached to a patient's arm, leg, chest, etc. in order to collect different parameters. Based upon the body part to which the patient monitoring device 304 is attached, the patient monitoring device may be differently configured, such as in accordance with a different template.

As shown at 1 in FIG. 5a, the patient monitoring device 304 may determine, e.g. automatically or semi-automatically, that it has been attached to a different body part for which the patient monitoring device is not yet configured. The patient monitoring device 304 may detect that it is directed to a different body part in various manners including, for example, information provided by the patient or medical profession taking care of the patient, information provided by a sensor, e.g., accelerometer, configured to detect the position of the measurement unit, e.g. based on the acceleration that is experienced, information about the length of a band used to attach the patient monitoring device to the patient, and/or information provided by sensor measurements that are configured to determine the position of the patient monitoring device. As an example of the manner in which the sensor measurements may identify the body part to which the patient monitoring device 304 is attached, the acceleration of the device is different and very distinguishable during specific movement patterns like walking when the unit is attached to the arm, wrist, hip, or chest. The patient monitoring device 304 can use the acceleration sensors to detect when the patient wearing the unit is moving, e.g. walking, and then correlate the acceleration data with the known acceleration patterns relevant for different body positions while moving. Similarly, the information from other sensors can be utilized as well to define the body position such as in the case when the patient monitoring device 304 can only be worn on an arm, chest, or lack of electrocardiograph (ECG) cables or ECG signals which can be used to define the body position. Also additional sensor information like the detected strap used to mount the device, can be utilized to identify the body part.

Once the patient monitoring device 304 detects that it has been attached to a different body part, the patient monitoring device is configured to transmit a message as shown at 1 to the computing device 302 indicating that the patient monitoring device is not properly configured for the body part to which it is now attached and providing an identifier of the patient monitoring device. The computing device 302 may receive the message from the patient monitoring device 304 and may then query its user for an indication of the body part to which the patient monitoring device is attached as shown at 2 and 3.

Once the position of the patient monitoring device 304 is identified, the computing device 302 of one example embodiment transmits a message to the cloud service 306 that identifies the patient monitoring device, such as by its identifier, and also indicates the body part, e.g., left arm, to which the patient monitoring device is now attached, as shown at 4a. Alternatively, the computing device 302 of another example embodiment may transmit a message to the patient monitoring device 304 that indicates the body part, e.g., left arm, to which the patient monitoring device is now attached and the patient monitoring device may, in turn, transmit a message to the cloud service 306 that identifies the patient monitoring device and the body part to which the patient monitoring device is attached, as shown in 4b. Regardless of the transmission path, the indication of the body part to which the patient monitoring device 304 is attached serves as the indication of the anticipated utilization of the patient monitoring device and is utilized by the cloud service 306 to identify the appropriate device configuration information, e.g., template.

In an embodiment in which the computing device 302 transmits a message to the cloud service 306 as shown at 4a informing the cloud service of the body part to which the patient monitoring device 304 is now attached, the cloud service may respond by transmitting a message to the computing device that provides the appropriate template, e.g., the template that provides the measurement set up for the "left arm". The computing device 302 may, in turn, forward this template to the patient monitoring device 304, as shown in 5a. Alternatively, in an embodiment in which the patient monitoring device 304 transmits a message to the cloud service 306 informing the cloud service of the body part to which it is now attached, the cloud service may respond directly to the patient monitoring device by transmitting a message to the patient monitoring device that provides the template appropriate for the particular body part as shown at 5b.

As shown in FIG. 5b, the cloud service 306 may store the measurement setup and configuration in the form of templates associated with different body positions. In this implementation, the information of the current measurement unit position and the matching template is transferred between the cloud service 306 and the patient monitoring device 304. The measurement templates can be also or alternatively stored within the computing device 302 or patient monitoring device 304. Based upon the device configuration information, such as the template, provided by the cloud service 306, the patient monitoring device 304 may be reconfigured so as to monitor the patient while attached to the respective body part in the desired manner. As described above, this reconfiguration of the patient monitoring devices 304, such as in an automatic fashion, increases the efficiency and accuracy with which patient monitoring devices may be reconfigured.

It will be understood that each step of the sequence diagrams, and combinations of steps in the diagrams, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by the memory device 204 of an apparatus employing an embodiment of the present invention and executed by the processor 202 of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, steps of the sequence diagrams support combinations of means for performing the specified functions and combinations of operations for performing the specified functions. It will also be understood that one or more steps of the sequence diagrams, and combinations of steps of the sequence diagrams, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
   receiving context information of a patient monitoring device, wherein the context information of the patient monitoring device comprises: i) a department, unit, or other environment within which the patient monitoring device is located, ii) information regarding a type, identification, and/or network address of the patient monitoring device, and iii) an indication of a body part of a patient to which the patient monitoring device is attached;
   determining to configure the patient monitoring device if the received context information of the patient monitoring device is different than a current context associated with the patient monitoring device;
   identifying device configuration information based on the received context information, wherein the device configuration information includes monitoring measurement parameters for the body part of the patient to which the patient monitoring device is attached; and
   causing provision of the identified device configuration information to facilitate monitoring measurement parameters for the body part of the patient to which the patient monitoring device is attached.

2. A method of claim 1, wherein receiving the context information of the patient monitoring device further comprises receiving information that defines the device configuration information that is to be provided.

3. A method of claim 1, further comprising:
   determining access rights to data generated by the patient monitoring device subsequently operating in accordance with the device configuration information; and
   providing an indication of the access rights.

4. A method of claim 1, wherein causing provision of the device configuration information comprises causing provision information that defines one or more of measurement parameters to be monitored by the patient monitoring device, measurement intervals at which the measurement parameters are to be monitored by the patient monitoring device or alert limits based upon the measurement parameters to be monitored by the patient monitoring device.

5. A method of claim 1, further comprising accessing the device configuration information by accessing cloud entity that stores or defines the device configuration information for a plurality of different configurations.

6. An apparatus comprising at least one processor and at least one memory storing computer program code, the at least one memory and the computer program code configured to, with the processor, cause the apparatus to at least:
   receive context information of a patient monitoring device, wherein the context information of the patient monitoring device comprises i) a department, unit, or other environment within which the patient monitoring device is located, ii) information regarding a type, identification, and/or network address of the patient monitoring device, and iii) an indication of a body part of a patient to which the patient monitoring device is attached;
   determine to configure the patient monitoring device if the received context information of the patient monitoring device is different than a current context associated with the patient monitoring device;
   identify device configuration information based on the received context information, wherein the device configuration information includes monitoring measurement parameters for the body part of the patient to which the patient monitoring device is attached; and
   cause provision of the identified device configuration information to facilitate monitoring measurement parameters for the body part of the patient to which the patient monitoring device is attached.

7. An apparatus of claim 6, wherein the at least one memory and the computer program code are configured to, with the processor, cause the apparatus to further receive information that defines the device configuration information that is to be provided.

8. An apparatus of claim 6, wherein the at least one memory and the computer program code are further configured to, with the processor, cause the apparatus to:

determine access rights to data generated by the patient monitoring device subsequently operating in accordance with the device configuration information; and provide an indication of the access rights.

9. An apparatus of claim 6, wherein the at least one memory and the computer program code are configured to, with the processor, cause the apparatus to cause provision of the device configuration information by causing provision of information that defines one or more of measurement parameters to be monitored by the patient monitoring device, measurement intervals at which the measurement parameters are to be monitored by the patient monitoring device or alert limits based upon the measurement parameters to be monitored by the patient monitoring device.

10. An apparatus of claim 6, wherein the at least one memory and the computer program code are configured to, with the processor, cause the apparatus to access the device configuration information by accessing cloud entity that stores or defines the device configuration information for a plurality of different configurations.

11. A method comprising:
receiving information regarding a configuration of a patient monitoring device, wherein the information regarding the configuration comprises an identifier associated with the patient monitoring device and device configuration information;
determining, based on the received information regarding the configuration of the patient monitoring device, whether to differently configure the patient monitoring device in accordance with context information of the patient monitoring device, the context information of the patient monitoring device comprises i) a department, unit, or other environment within which the patient monitoring device is located, ii) information regarding a type, identification, and/or network address of the patient monitoring device, and iii) an indication of a body part of a patient to which the patient monitoring device is attached; and
in an instance in which the patient monitoring device is to be differently configured based on the context information of the patient monitoring device being different than a current context associated with the patient monitoring device, causing information related to the device configuration information associated with the context information to be provided to facilitate monitoring measurement parameters for the body part of the patient to which the patient monitoring device is attached.

12. A method according to claim 11, wherein the device configuration information defines one or more of measurement parameters to be monitored by the patient monitoring device, measurement intervals at which the measurement parameters are to be monitored by the patient monitoring device or alert limits based upon the measurement parameters to be monitored by the patient monitoring device.

13. A method according to claim 11, further comprising receiving and subsequently operating in accordance with access rights to data generated by the patient monitoring device subsequently operating in accordance with the device configuration information.

14. A method according to claim 11, wherein causing the information related to the device configuration information associated with the context information to be provided comprises causing the information to be provided to a cloud entity that stores and/or defines device configuration information for different configurations of the patient monitoring device or to the patient monitoring device.

15. An apparatus comprising at least one processor and at least one memory storing computer program code, the at least one memory and the computer program code configured to, with the processor, cause the apparatus to at least:
receive information regarding a configuration of a patient monitoring device, wherein the information regarding the configuration comprises an identifier associated with the patient monitoring device and device configuration information;
determine, based on the received information regarding the configuration of the patient monitoring device, whether to differently configure the patient monitoring device in accordance with context information of the patient monitoring device, the context information of the patient monitoring device comprises i) a department, unit, or other environment within which the patient monitoring device is located, ii) information regarding a type, identification, and/or network address of the patient monitoring device, and iii) an indication of a body part of a patient to which the patient monitoring device is attached; and
in an instance in which the patient monitoring device is to be differently configured based on the context information of the patient monitoring device being different than a current context associated with the patient monitoring device, cause information related to the device configuration information associated with the context information to be provided to facilitate monitoring measurement parameters for the body part of the patient to which the patient monitoring device is attached.

16. An apparatus according to claim 15, wherein the device configuration information defines one or more of measurement parameters to be monitored by the patient monitoring device, measurement intervals at which the measurement parameters are to be monitored by the patient monitoring device or alert limits based upon the measurement parameters to be monitored by the patient monitoring device.

17. An apparatus according to claim 15, wherein the at least one memory and the computer program code are further configured to, with the processor, cause the apparatus to receive and subsequently operate in accordance with access rights to data generated by the patient monitoring device subsequently operating in accordance with the device configuration information.

18. An apparatus according to claim 15, wherein the at least one memory and the computer program code are configured to, with the processor, cause the apparatus to cause the information related to the device configuration information associated with the context information to be provided by causing the information to be provided to a cloud entity that stores or defines device configuration information for different configurations of the patient monitoring device or to the patient monitoring device.

19. A method according to claim 11, wherein determining, based on the received information regarding the configuration of the patient monitoring device, whether to differently configure the patient monitoring device comprises determining the body part of the patient to which the patient monitoring device is attached based on an acceleration of the patient monitoring device, information about a length of a band used to attach the patient monitoring device to the patient, or information provided by one or more sensors configured to determine a position of the patient monitoring device.

20. An apparatus according to claim 15, wherein the at least one memory and the computer program code are configured to, with the processor, cause the apparatus to determine, based on the received information regarding the configuration of the patient monitoring device, whether to differently configure the patient monitoring device by determining the body part of the patient to which the patient monitoring device is attached based on an acceleration of the patient monitoring device, information about a length of a band used to attach the patient monitoring device to the patient, or information provided by one or more sensors configured to determine a position of the patient monitoring device.

* * * * *